(12) United States Patent
Etters (10) Patent No.: US 9,375,187 B2
(45) Date of Patent: Jun. 28, 2016

(54) MODULAR PATIENT HANDLING SYSTEM FOR MEDICAL IMAGING APPARATUS

(75) Inventor: Bradley Etters, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 658 days.

(21) Appl. No.: 13/526,701

(22) Filed: Jun. 19, 2012

(65) Prior Publication Data

US 2013/0334439 A1    Dec. 19, 2013

(51) Int. Cl.
*A61G 7/10* (2006.01)
*A61B 6/03* (2006.01)
*A61B 6/04* (2006.01)

(52) U.S. Cl.
CPC .............. *A61B 6/03* (2013.01); *A61B 6/0407* (2013.01); *A61G 7/1032* (2013.01)

(58) Field of Classification Search
CPC ............ A61B 5/05; A61B 5/055; A61B 6/03; A61B 6/04; A61B 5/00
USPC ......................................................... 600/407
See application file for complete search history.

(56) References Cited

U.S. PATENT DOCUMENTS

| 4,131,802 | A | * | 12/1978 | Braden | A61B 6/0442 250/363.02 |
| 6,217,214 | B1 | * | 4/2001 | Cabral | A61B 6/0421 378/196 |
| 2003/0078489 | A1 | * | 4/2003 | DeSilets et al. | 600/407 |
| 2005/0005356 | A1 | * | 1/2005 | Zacharopoulos | A61B 6/04 5/601 |
| 2006/0289275 | A1 | * | 12/2006 | Lemke | B65G 21/14 198/460.2 |
| 2007/0287908 | A1 | * | 12/2007 | Karl | A61B 5/0555 600/415 |
| 2011/0092792 | A1 | | 4/2011 | Birman | |
| 2012/0049084 | A1 | * | 3/2012 | Abenaim | A61B 6/0407 250/454.11 |

* cited by examiner

*Primary Examiner* — Tse Chen
*Assistant Examiner* — Charles G Chiang
(74) *Attorney, Agent, or Firm* — Peter Kendall (57) ABSTRACT

A patient table mounts to a patient imaging apparatus support base. When attached to first and second support ends of an imaging apparatus, the patient table has a generally planar patient support adapted for spanning the imaging apparatus field of view (FOV), and is analogous to a beam spanning the FOV. The beam-like patient support has sufficient rigidity for supporting and imaging a patient placed thereupon without any additional external support columns affixed to the imaging room floor, as was utilized in previously existing imaging apparatus. Elimination of external patient table supports reduces imaging apparatus installation complexity and costs, frees up floor space, and facilitates easier patient transfer to the imaging apparatus.

6 Claims, 6 Drawing Sheets

MODULAR PATIENT HANDLING SYSTEM FOR MEDICAL IMAGING APPARATUS

BACKGROUND OF THE DISCLOSURE

1. Field of the Invention

The invention relates to a patient handling system for medical diagnostic imaging systems. More particularly the invention relates to a modular patient handling system with a patient table affixed to and spanning a diagnostic imaging system support base within the imaging field of view, and including a conveyor for transporting patients in and out of the imaging system field of view.

2. Description of the Prior Art

Figure 1:
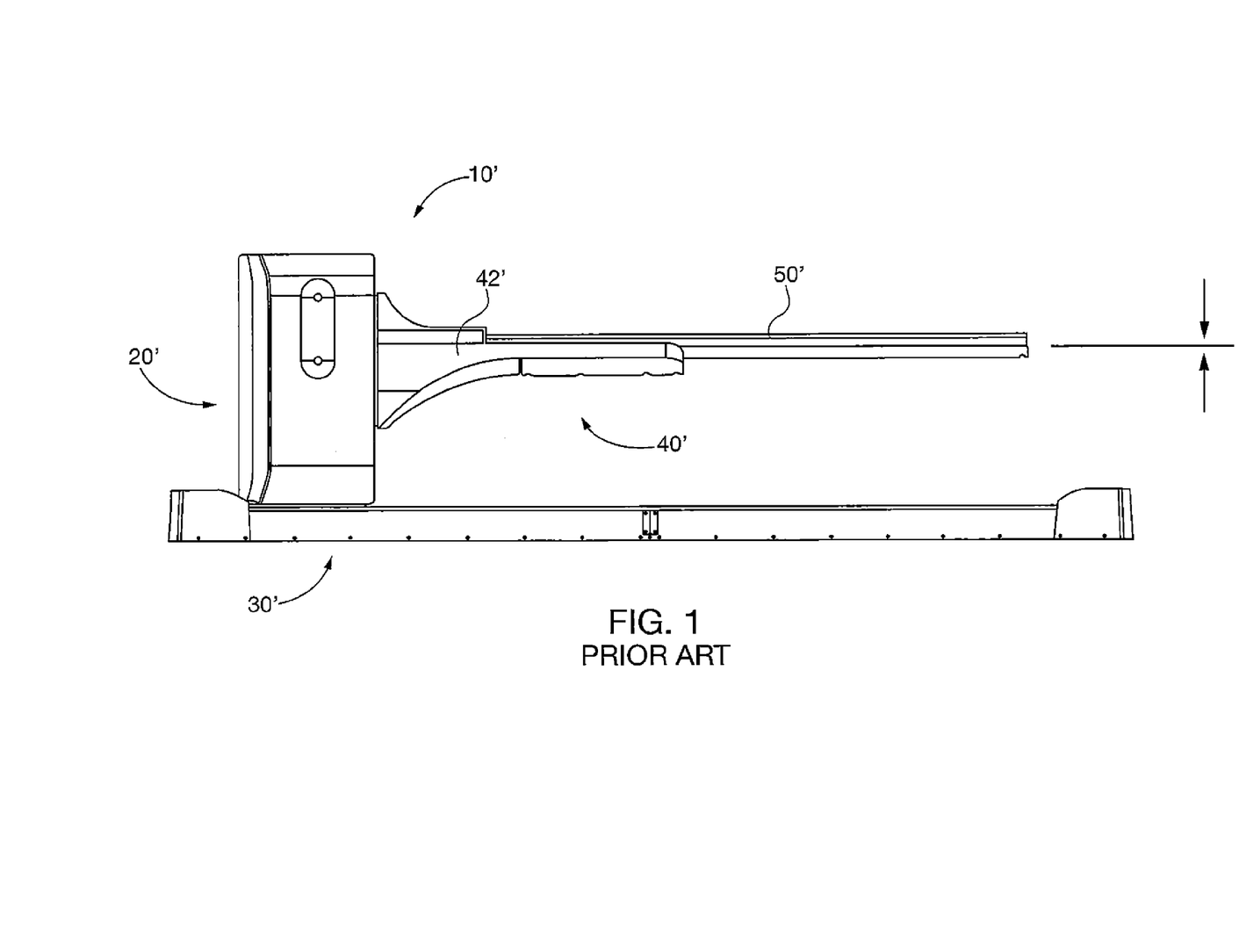
FIG. 1 shows a side elevational view of an known medical imaging apparatus.
Figure 2:
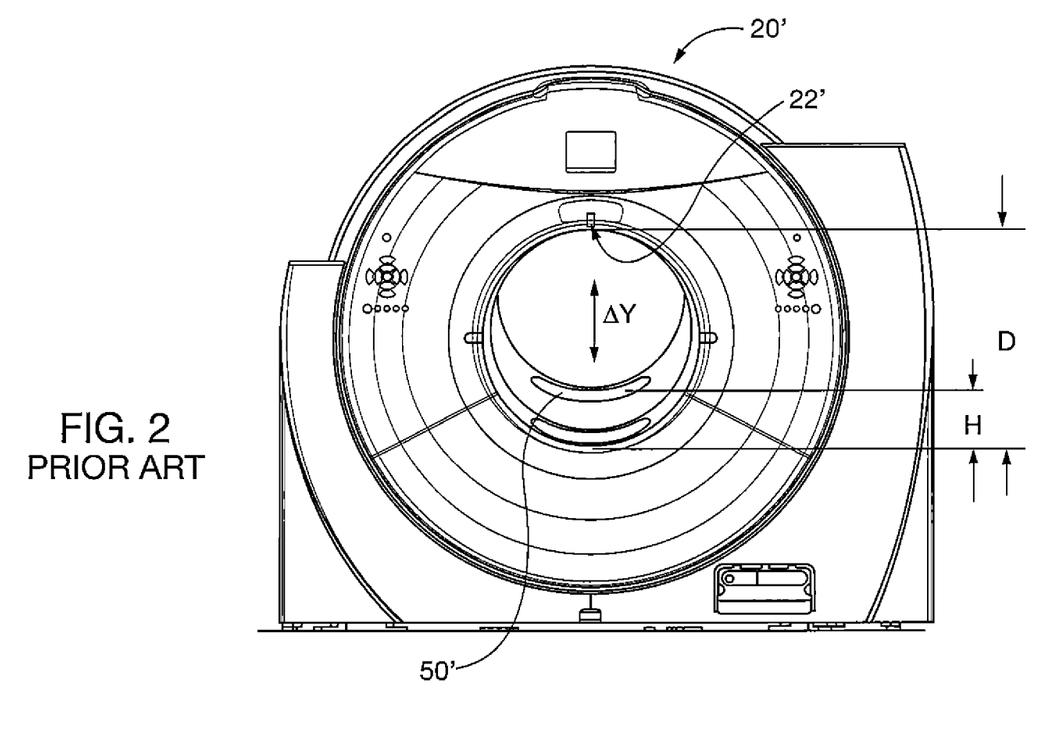
FIG. 2 shows an axial end elevational view of a known medical imaging apparatus.

As shown in FIGS. 1 and 2, existing medical diagnostic imaging apparatus 10' includes an imaging system 20' with a field of view (FOV) established within patient receiving tunnel or bore 22'. Exemplary imaging system modalities include X-ray radiography or fluoroscopy, computed tomography (CT), positron emission tomography (PET), single photon emission computed tomography (SPECT), ultrasound, or magnetic resonance imaging (MRI). Existing diagnostic imaging apparatus 10' may incorporate more than one imaging modality: often oriented with adjoining fields of view within the patient receiving bore 22'.

The imaging apparatus 10' includes a support base 30' that is rigidly affixed to an imaging center floor. The floor is often constructed of reinforced poured concrete. During installation of an imaging apparatus 10', the support base 30' is often affixed to a floor at designated mounting points by precision drilling of an array of holes into the concrete, followed by precise insertion and embedding of threaded rods into the holes with epoxy or other permanent bonding media. The support base 30' structure is then affixed to floor mounting points by engaging the embedded threaded rods with mating threaded fasteners. Creation of a precision array of holes and subsequent threaded rod embedding is complex and time consuming. Imaging apparatus 10' installation effort is roughly proportional to the number of mounting points that must be installed for a support base 30' footprint. The support base 30' of FIG. 1 includes a separate and distinct floor-mounted extension portion under cantilevered patient table 40', in order to counteract deflection forces caused when a patient is placed on the table. The floor-mounted extension portion of support base 30' consumes additional floor space that is not needed for support of the imaging system 20' and inhibits maneuvering of patient gurneys or transport beds close to the imaging apparatus 10'.

The patient table 40' includes a cantilevered table frame 42' mounted external the imaging system 20' and its related portion of the support base 30'. The table frame 42' includes a rail structure (not shown) for engagement with a reciprocating/translating patient bed 50' that is cantilevered into the patient bore 22'. Thus the frame 42' is in effect a cantilever beam that is in turn supported from the oppositely directed cantilevered patient table 40'. The patient table 40' a vertical height adjustment capability that is schematically shown as ΔY in FIG. 2. The patient bed 50' is translatable horizontally and vertically under control of a servo motor system (not shown) within the imaging system bore 22', on the frame 42' rails, so that the patient can be aligned selectively within the field of view. The table frame 42', its rail structure, vertical height adjustment and the reciprocating patient bed 50' project a minimum height H within the diameter D of the patient bore 22' and thereby adversely reduces available inspection volume within the patient bore (i.e., it reduces the volume in which a patient can be oriented). Reduced available inspection volume reduces patient maneuvering flexibility within the patient bore 22'—especially for larger patients.

Patient weight impacts cantilever deflection loads on the patient table 40'. Excessive weight deflection loads can cause unwanted vertical movements (often referred to as "porpoising") that can cause image distortion during diagnostic scanning procedures. Weight deflection is often countered in patient table 40' design by utilization of larger and higher strength components within the imaging system 20' field of view that may also adversely cause so-called "ghost" or "artifact" image distortion.

During an imaging procedure with the imaging apparatus 10' a portion of a patient that is being imaged is inserted into the patient bore 22' with the patient in a generally supine position. The patient is transferred to the imaging apparatus 10' while the patient bed 50' is extended distally from the patient bore 22', as shown in FIG. 1. When initially transferred to the patient bed 50' a relatively ambulatory patient is seated on a lateral edge of the bed and then oriented in a supine position so that the bed and patient thereafter can be translated into the patient bore 22'. Non-ambulatory patients must be transferred laterally from a gurney or other mobile bed to the patient bed 50', with the assistance of medical personnel. Patient transfers to the imaging system 10' patient bed 50'—whether ambulatory or non-ambulatory—can cause patient discomfort and are relatively laborious for assisting medical personnel.

A proposed patient positioning solution in U.S. Patent Publication No. US 2011/0092792, published Apr. 21, 2011, incorporates a motorized conveyor belt oriented through both sides of an imaging system bore. The conveyor belt is placed on a support platform that bridges the imaging system bore and is supported vertically on both sides of the bore by external columns that are affixed to the imaging room floor. External columns require the aforementioned construction costs and efforts necessary for affixing them to the imaging room floor. The external columns also have the aforementioned problems of consuming floor space and inhibiting maneuvering of patient transport beds proximal to the imaging apparatus. The known conveyor belt construction has the same aforementioned patient transferring challenges regarding ambulatory and non-ambulatory patient placement on the conveyor belt.

Thus, a need exists in the art for a medical diagnostic imaging apparatus patient table that is capable of supporting a larger patient weight load without causing excessive load deflection within or external the patient bore that can adversely impact image quality.

Another need exists in the art for a medical diagnostic imaging apparatus patient table that is capable of supporting a larger patient weight load without increasing component size within the imaging field of view that might otherwise adversely impact image quality.

An additional need exists in the art for a medical diagnostic imaging apparatus patient table that increases available patient imaging volume within a given size imaging system patient bore.

Yet another need exists in the art for a medical diagnostic imaging apparatus patient table that does not require installation and affixation of dedicated patient table external support structure to the imaging room floor.

Another need exists in the art for a medical diagnostic imaging apparatus patient table that facilitates easier transfer of ambulatory or non-ambulatory patients to the table.

SUMMARY OF THE INVENTION

Accordingly, an object of the invention is to create a medical diagnostic imaging apparatus patient table that is capable of supporting a larger patient weight load without causing excessive load deflection within or external the patient bore that can adversely impact image quality.

Another object of the invention is to create a medical diagnostic imaging apparatus patient table that is capable of supporting a larger patient weight load without increasing component size within the imaging field of view that can adversely impact image quality.

An additional object of the invention is to create a medical diagnostic imaging apparatus patient table that increases available patient imaging volume within a given size imaging system patient bore.

Yet another object of the invention is to create a medical diagnostic imaging apparatus patient table that does not require installation and affixation of dedicated patient table external support structure to the imaging room floor.

Another object of the invention is to create a medical diagnostic imaging apparatus patient table that facilitates easier transfer of ambulatory or non-ambulatory patients to the table.

These and other objects are achieved in accordance with the present invention by a diagnostic imaging apparatus patient table that is adapted for selective attachment to and detachment from a patient imaging apparatus having an existing support base that is already affixed on a floor, where the support base has first and second support ends. The imaging apparatus further has an imaging system that is coupled to the support base, and defines a field of view (FOV). When attached to an imaging apparatus, the patient table of the present invention has a generally planar patient support adapted for spanning the imaging apparatus FOV and attaches to the existing first and second support ends. The patient support is analogous to a beam spanning the FOV that is affixed to both ends of the support base. Thus the beam-like patient support has sufficient rigidity for supporting and imaging a patient placed thereupon without any additional external support structure, such as the known external extended support base or external support columns affixed to the imaging room floor utilized in previously existing imaging apparatus. Elimination of external patient table supports reduces imaging apparatus installation complexity and costs, frees up floor space, and facilitates easier patient transfer to the imaging apparatus.

The present invention facilities direct transfer of a supine patient from a transportable patient bed to the patient table, simply by axially co-aligning the transportable patient bed with the patient table and thereafter sliding the patient onto the patient table. Embodiments of the present invention also include an interlock for coordinating conveyor speeds of the patient table and a transportable patient bed with a similar motorized conveyor surface.

An embodiment of the present invention features a patient imaging apparatus, including a support base for affixation on a floor, having first and second support ends. An imaging system is coupled to the support base, defining a field of view (FOV). A patient table is supportively coupled to the support base first and second support ends, spanning the support ends and the FOV. The table has sufficient rigidity for supporting and imaging a patient placed thereupon without additional support structure. The patient table has a movable table conveyor on the table, for selectively translating and positioning a patient placed thereupon within the FOV.

Another embodiment of the present invention features a patient imaging apparatus, including a support base for affixation on a floor, having first and second support ends. An imaging system is coupled to the support base, defining a field of view (FOV). A patient table is supportively coupled to the support base first and second support ends, spanning the support ends and FOV. The table has sufficient rigidity for supporting and imaging a patient placed thereupon without additional support structure. A powered vertical translation mechanism is coupled to the table and the support base for vertically translating the table. A powered table conveyor is oriented on the table, for translating and positioning a patient placed thereupon within the FOV. Further in this embodiment, a conveyor motor is coupled to the table and a vertical translation motor is coupled to the vertical translation mechanism, respectively for translating the table conveyor and table within the FOV. A patient translation controller is coupled to the conveyor and vertical translation motors, for causing the motors to translate the table conveyor to a selected position in the FOV. Patient transfer may be further facilitated by addition of a movable patient transport bed having a movable transport bed conveyor aligned with a long axis of the bed, for transferring a patient placed thereon off an end of the bed onto the table conveyor. A bed conveyor motor is coupled to the transport bed, for translating the bed conveyor. In this embodiment an interlock couples the bed conveyor motor to the patient translation controller, for coordinating translation of the respective table and bed conveyors.

The present invention additionally features a modular patient table apparatus adapted for selective attachment to and detachment from a patient imaging apparatus having a support base for affixation on a floor. The support base has first and second support ends. An imaging system is coupled to the support base, defining a field of view (FOV). This embodiment patient table has a generally planar patient support adapted for spanning an imaging apparatus first and second support ends of a support base and the FOV. The patient support has sufficient rigidity for supporting and imaging a patient placed thereupon without additional external support structure. In this embodiment first and second vertical supports project downwardly from the patient support, and are adapted for selective coupling to the respective first and second support ends of an imaging apparatus support base with removable fasteners, so that the table is selectively removable from the imaging apparatus as a modular structure. A movable table conveyor is oriented on the patient support, and is adapted for translating a patient placed thereupon within an imaging apparatus FOV.

The objects and features of the present invention may be applied jointly or severally in any combination or sub-combination by those skilled in the art.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

After considering the following description, those skilled in the art will clearly realize that the teachings of the present invention can be readily utilized in a modular patient handling system for medical imaging apparatus that includes a patient table, which mounts to a an existing patient imaging apparatus support base. When attached to first and second support ends of an imaging apparatus, the patient table has a generally planar patient support adapted for spanning the imaging apparatus field of view (FOV), and is analogous to a beam spanning the FOV. The beam-like patient support has sufficient rigidity for supporting and imaging a patient placed thereupon without any additional external support columns affixed to the imaging room floor, as were used in previously existing imaging apparatus. Elimination of external patient table supports reduces imaging apparatus installation complexity and costs, frees up floor space, and facilitates easier patient transfer to the imaging apparatus.

Figure 3:
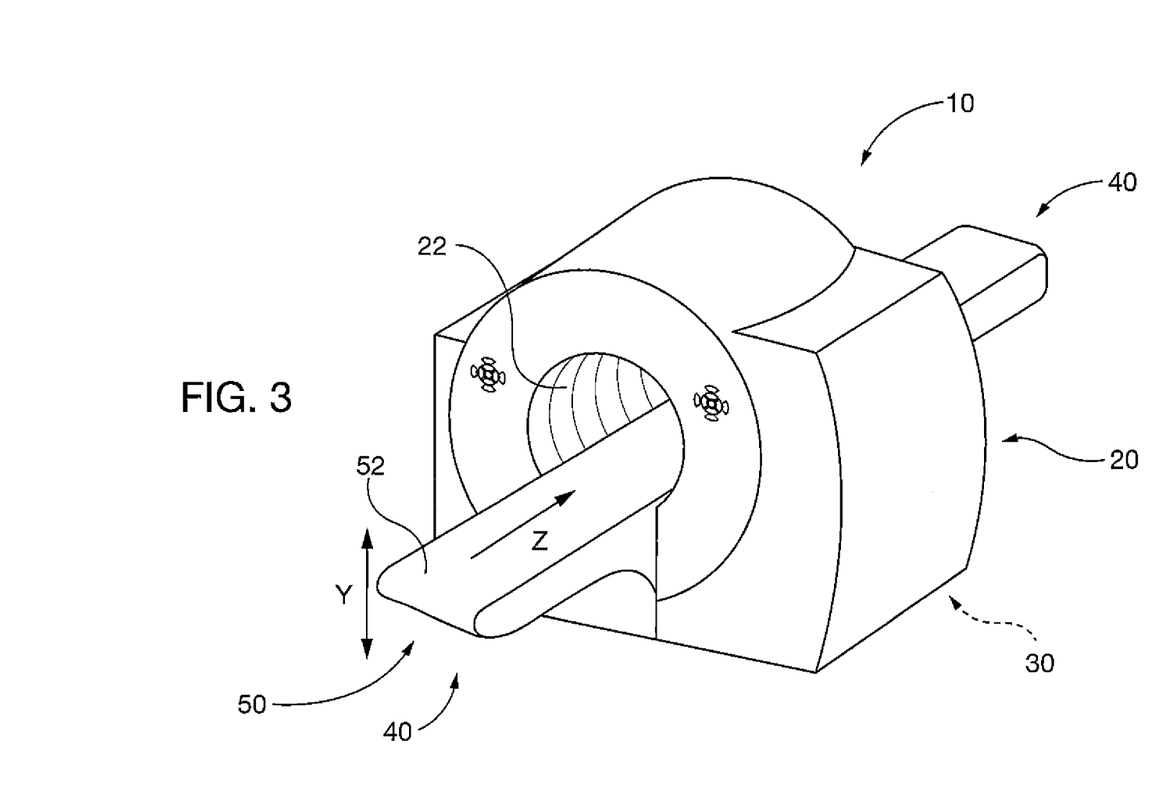
FIG. 3 shows a perspective elevational view of an embodiment of a medical imaging apparatus including the modular patient handling system of the present invention.
Figure 4:
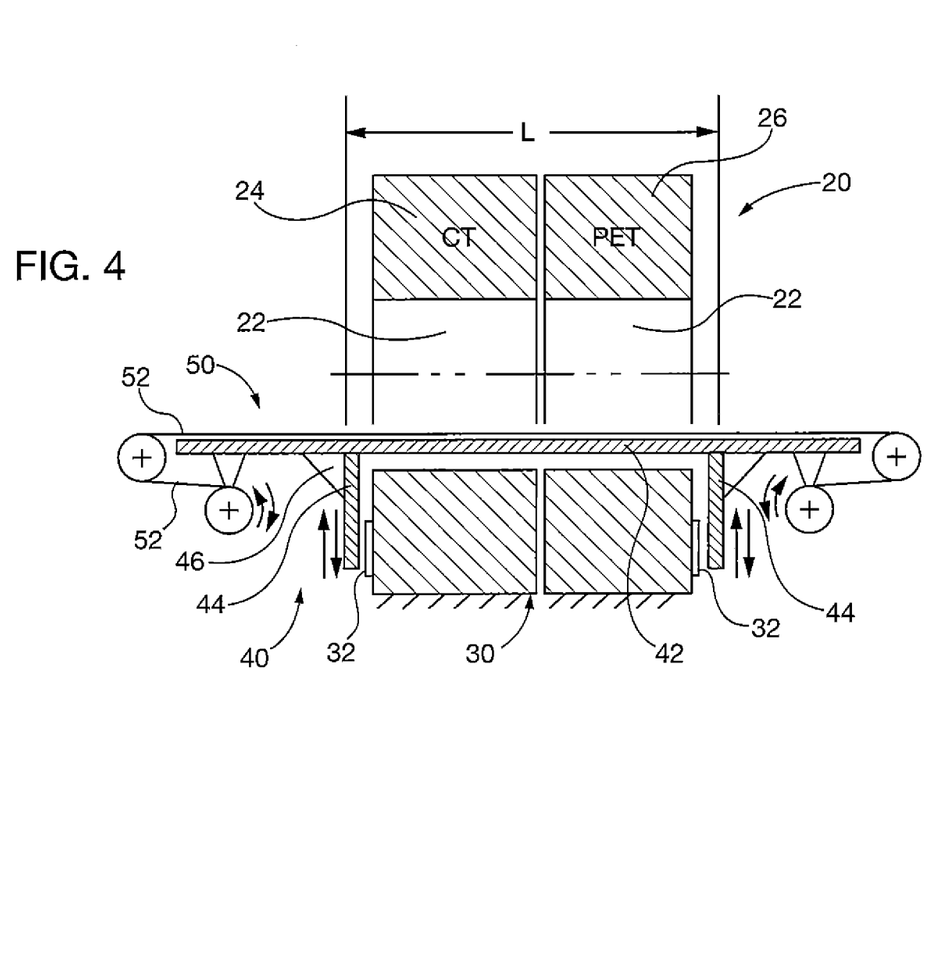
FIG. 4 shows an schematic axial elevational cutaway view of the apparatus of FIG. 3.

FIGS. 3 and 4 show a medical imaging apparatus 10, including an imaging system 20 and patient bore 22 that define an imaging field of view (FOV) therein. The imaging system may comprise one or more imaging modalities, including by way of example X-ray radiography or fluoroscopy, computed tomography (CT), positron emission tomography (PET), single photon emission computed tomography (SPECT), ultrasound, or magnetic resonance imaging (MRI). The exemplary imaging system 10 has CT 24 and PET 26 modalities that are oriented with adjoining fields of view within the patient receiving bore 22. Thus a patient may undergo two separate imaging procedures by moving him or her axially within the receiving bore 22.

The imaging system 10 is supported on a support base 30 that is customarily rigidly affixed to the imaging room floor by the aforementioned affixation method. The support base has axial ends 32 that generally bound the axial ends of the imaging system 20 patient bore 22. A patient is supported by and positioned within the imaging apparatus 10 by a patient handling system 40 that provides axial-horizontal and vertical positioning as shown schematically by the respective Z and Y arrows in FIG. 3.

Figure 5:
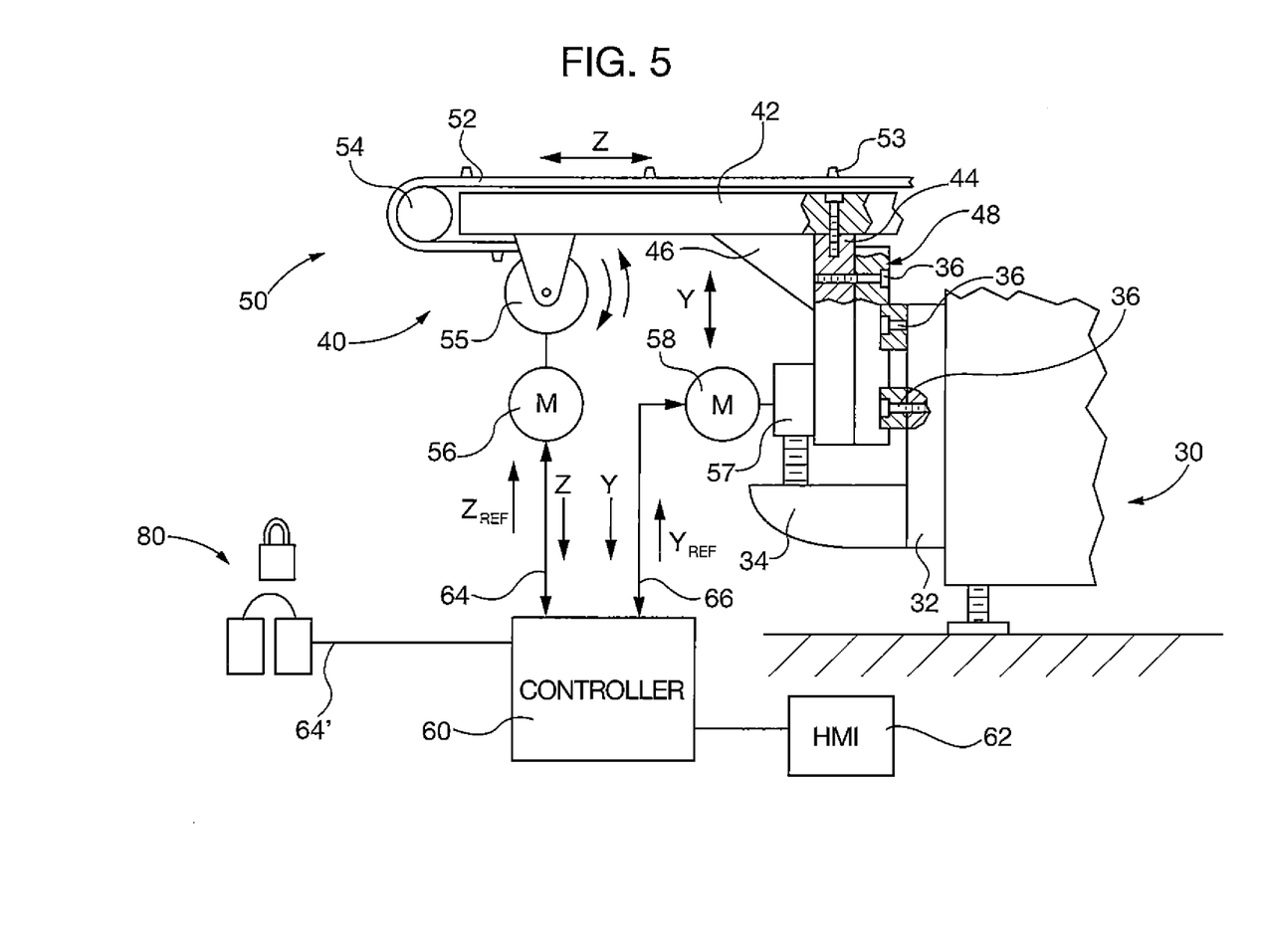
FIG. 5 is a schematic elevational view of an embodiment of the horizontal and vertical patient positioning system of the patient handling system of FIGS. 3 and 4.

As shown in FIGS. 4 and 5, the patient handling system 40 includes a generally planar patient table 42 from which pairs of first and second vertical supports 44 and reinforcing gussets 46 that are affixed and project downwardly from the table. While the patient table 42 is schematically shown as a flat planar sheet spanning the imaging system patient bore 22, other multi-dimensional structural shapes and materials may be utilized that provided needed deflection support yet that minimize likelihood of ghost or artifact image distortion. The first and second vertical supports 44 are adapted for selective coupling and slidable mounting to the respective first and second support ends 32 of the imaging apparatus support base 30 with removable fasteners 36, so that the table is selectively removable from the imaging apparatus as a modular structure. The first and second vertical supports 44 are affixed to vertically oriented and slidable linear bearings 48 with known bearing block and rail construction. The bearings 48 on each end of the table first and second vertical supports 44 are in turn affixed to the respective first and second support ends 32 in which fasteners 36 are restrained, so that the patient table 42 and entire patient handling system 40 is capable of selective vertical translation on the slidable linear bearings for patient positioning, as will be described in greater detail below.

As shown in FIG. 4, the modular patient table 42, with its vertical supports 44, gussets 46 are collectively referred to as a patient support 50. The patient support 50 effectively functions as a structural beam supported by the first and second support ends of the existing imaging apparatus support structure 30, and is capable of sustaining a greater patient weight load without permitting excessive deflection that can reduce image quality. The beam-like patient support 50 has sufficient rigidity for supporting and imaging a patient placed thereupon without any additional external support columns affixed to the imaging room floor, as was utilized in previously existing imaging apparatus. Elimination of auxiliary external patient table support columns reduces installation/construction costs associated with drilling and affixing those external support columns to the floor. Attaching the patient support 50 directly to the apparatus support structure 30 rather than to outlying external patient table support columns results in a shorter span distance L needed to support patient weight load, and hence less deflection per unit length of the patient support 50. The shorter span length L of the patient support 50 to the patient support structure 30 allows use of less structural mass as well as non-metallic materials that might otherwise negatively impact image quality "artifacts" or "ghosts". External patient table support column elimination frees up floor space and allows easier patient access to the patient handling system 40 during patient transfer to or from the imaging apparatus 10.

As shown in FIG. 5, the patient handling system 40 selectively positions a patient horizontally-axially within the imaging apparatus 10 field of view by motorized table conveyor 52 that is mounted to the patient support 50 on conveyor rollers 54. The conveyor 52 optionally may include cleats 53 for interlocking with corresponding slots in known patient head supports and the like, to aid in positional and motion accuracy. Conveyor winding drum 55, powered by motor 56, selectively translates the conveyor 52 along the axial path Z within the imaging system 20 field of view. The table conveyor 52 positions a patient vertically within the imaging apparatus 10 field of view by a powered vertical translation mechanism, shown as an exemplary screw drive 57 powered by motor 58. A screw drive 57 is coupled to each pedestal 34 of the respective first and second support ends 32, and the respective first and second vertical supports 44 of the patient table 42. Patient translation controller 60, which for example may be a stand-alone motion control sub-system or an integrated motion control system within the imaging apparatus, causes the motors 56 and 58 respectively to translate the patient handling system 40 to desired positions for patient loading and positioning within the imaging apparatus 10 field of view. The controller 60 is communicatively coupled to the conveyor motor 56 via a known communications pathway 64 and issues axial-horizontal translation commands $Z_{REF}$ to cause motor rotation. A motor shaft encoder or other positional feedback device sends motor shaft rotational position information Z to the controller 60. The controller 60 associates motor shaft rotation position information Z with actual position/motion of the conveyor 52. As noted, other known positional feedback devices may be substituted for the exemplary motor shaft encoder. Auxiliary feedback componentry may be employed to further enhance the desired motion control. Similarly the controller issues vertical translation commands $Y_{REF}$ to the vertical translation motor 58 and receives motor shaft rotational position infottnation Y from an encoder or other positional feedback device associated with that motor. The controller 60 associates motor shaft rotation position information Y with actual vertical position/motion of the patient support 50.

Figure 6:
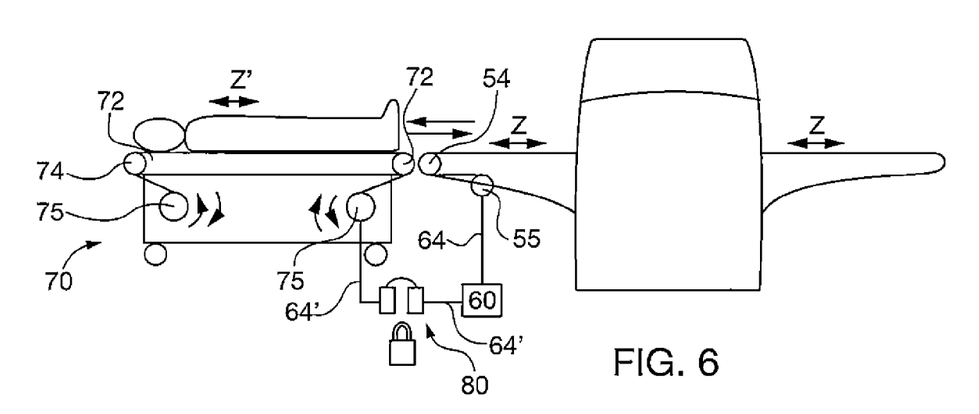
FIG. 6 is a side elevational view of the patient handling system of FIG. 3 along with a movable patient transport bed having a conveyor whose translation motion is coordinated with that of the table conveyor.
Figure 7:
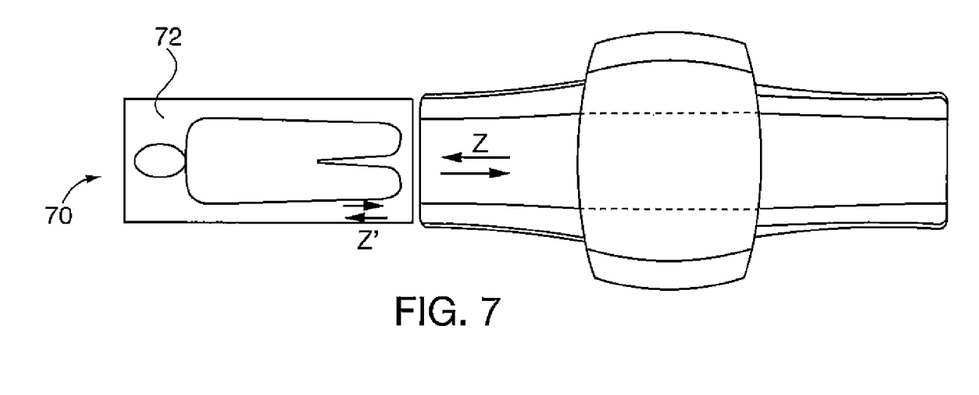
FIG. 7 is a top plan view of patient handling system and patient transport bed of FIG. 6.

The beam-like structural mounting of the patient support 50, with rigid affixation to the imaging apparatus 10 support base 30 also facilitates use of cantilevered ends on one or both ends of the patient handling system 40, without undue deflection "porpoiseing" of those ends that was associated with the imaging system 10' of FIGS. 1 and 3. The cantilevered ends in turn facilitate easier patient loading, as shown in FIGS. 6 and 7. The patient handling system of the present invention even facilitates direct axial loading supine patients directly from a transportable patient bed, whether the patient is ambulatory or non-ambulatory. The free-standing cantilevered ends of the present patient handling system 40 allow close access of a head or foot end of a patient bed to the conveyor 52. When the bed is positioned in abutting relationship with the conveyor end 52 the patient can be manually transferred to the imaging apparatus from either end thereof by medical caregivers. Alternatively, as shown in FIGS. 6 and 7 a movable patient transport bed 70 may be provided with a movable transport bed conveyor 72 that is affixed to the bed by rollers 74 and powered by a bed conveyor motor and motorized drum 75, similar to the imaging apparatus table conveyor 52. Advantageously an electrical or electromechanical interlock 80 may be provided that couples the respective table and transport bed motorized conveyor drums 55, 75 to the patient translation controller 60 via respective communication pathways 64, 64' for coordinated translation of the respective patient table and transport bed conveyors 52, 72. In this way a patient can be transported in a supine position from the bed 70 conveyor 72 directly and seamlessly to the table conveyor 52 of the patient handling system 40 with minimal effort and discomfort.

Although various embodiments, which incorporate the teachings of the present invention, have been shown and described in detail herein, those skilled in the art can readily devise many other varied embodiments that still incorporate these teachings.

What is claimed is:

1. A patient imaging apparatus, comprising:
   a support base for affixation on a floor, the support base having first and second vertical supports with respective inboard and outboard sides;
   an imaging system, including a patient bore that defines a bore axis and first and second axial bore ends, coupled to the support base between the respective inboard sides of the first and second vertical supports, the imaging system defining a field of view (FOV);
   a first slidable linear bearing, defining a vertically oriented translation axis, the first bearing having an inboard side coupled to the outboard side of the first vertical support by selectively removable first fasteners, which pass there through and engage the first vertical support, the first bearing having an outboard side;
   a first vertical patient table support, coupled to the outboard side of the first slidable linear bearing by selectively removable second fasteners;
   a first powered vertical translation mechanism, coupled to the first vertical patient table support and the outboard side of the first vertical support, for vertically translating the first vertical patient table support along the vertical translation axis of the first bearing;
   a second slidable linear bearing, defining a vertically oriented translation axis, the second bearing having an inboard side coupled to the outboard side of the second vertical support by selectively removable third fasteners, which pass there through and engage the second vertical support, the second bearing having an outboard side;
   a second vertical patient table support, coupled to the outboard side of the second slidable linear bearing by selectively removable fourth fasteners;
   a second powered vertical translation mechanism, coupled to the second vertical patient table support and the outboard side of the second vertical support, for vertically translating the second vertical patient table support along the vertical translation axis of the second bearing;
   a modular patient support apparatus, for selective attachment to and detachment from the respective first and second vertical patient table supports by fifth fasteners, the support apparatus having:
      an elongated patient table spanning the support base first and second vertical supports through the patient bore first and second axial bore ends and FOV, the patient table having sufficient rigidity for supporting and imaging a patient placed thereupon without additional support structure between the first and second vertical supports; and
      a movable table conveyor on the patient table, having a conveyor translation axis parallel with the corresponding patient bore axis, for translating a patient placed thereupon through the imaging apparatus first axial bore end to the second bore end within the FOV.

2. The apparatus of claim 1, wherein the table further comprises at least one cantilevered end projecting away from a corresponding support base first or second vertical support, outboard at least one of the patient bore first and second axial bore ends, and including the table conveyor, upon coupling the table to an imaging apparatus.

3. The apparatus of claim 1, wherein the table further comprises first and second cantilevered table ends that upon coupling the table to a corresponding imaging apparatus project away from the support base first and second vertical supports on opposite ends of the field of view, outboard both of the patient bore first and second axial bore ends, and including the table conveyor.

4. The apparatus of claim 1, further comprising:
   a powered table conveyor;
   a conveyor motor coupled to the table and respective first and second vertical translation motors coupled to the respective first and second vertical translation mechanisms, for translating the table conveyor and table within the imaging apparatus FOV; and
   a patient translation controller, coupled to the conveyor and vertical translation motors.

5. The apparatus of claim 4, further comprising:
   an interlock coupled to the patient translation controller; and
   a movable patient transport bed having:
      a movable transport bed conveyor having a bed conveyor translation axis aligned with a long axis of the bed;
      a bed conveyor motor coupled to the transport bed, for translating the bed conveyor;
   said interlock selectively coupled to the bed conveyor motor, for transferring a patient placed on the bed in abutting alignment with the table conveyor off an end of the bed onto the table conveyor, so that the patient translation controller is capable of coordinating translation of the respective table and bed conveyors.

6. The apparatus of claim 1, the first, second, third, fourth and fifth fasteners comprising threaded fasteners.

\* \* \* \* \*